United States Patent
Roberge et al.

(10) Patent No.: US 8,198,487 B2
(45) Date of Patent: Jun. 12, 2012

(54) METHOD FOR LITHIUM EXCHANGE REACTIONS

(75) Inventors: Dominique Roberge, Sirre (CH); Wilhelm Quittmann, Visp (CH); Markus Eyholzer, Glis (CH); Bertin Zimmermann, Brig-Glis (CH); Fabio Rainone, Visp (CH)

(73) Assignee: Lonza AG, Basel (CH)

( * ) Notice: Subject to any disclaimer, the term of this patent is extended or adjusted under 35 U.S.C. 154(b) by 297 days.

(21) Appl. No.: 12/524,910

(22) PCT Filed: Feb. 1, 2008

(86) PCT No.: PCT/EP2008/000808
§ 371 (c)(1),
(2), (4) Date: Jan. 14, 2010

(87) PCT Pub. No.: WO2008/095646
PCT Pub. Date: Aug. 14, 2008

(65) Prior Publication Data
US 2010/0113839 A1    May 6, 2010

(30) Foreign Application Priority Data

Feb. 6, 2007 (EP) .................................. 07002522

(51) Int. Cl.
*C07C 29/40* (2006.01)
(52) U.S. Cl. ........................................................ 568/814
(58) Field of Classification Search ....................... None
See application file for complete search history.

(56) References Cited

U.S. PATENT DOCUMENTS 6,616,859 B1 * 9/2003 Nickel et al. ............. 252/182.12

OTHER PUBLICATIONS

Database CAPLUS on STN, Acc. No. 2005:874816, Hikage et al., AIChE Spring National Meeting, conference proceedings, Atlanta, GA, USA, Apr. 10-14, 2005, 132F/1 (abstract).*
Database CAPLUS on STN, Acc. No. 2005:75241, Schmalz et al., EP 1500649 A1 (Jan. 26, 2005) (abstract).*
Database CAPLUS on STN, Acc, No. 2006:941050, Hikage et al., JP 2006241065 A (Sep. 14, 2006) (abstract).*

* cited by examiner

*Primary Examiner* — Brian J Davis
(74) *Attorney, Agent, or Firm* — Hoffmann & Baron, LLP

(57) ABSTRACT

The present invention relates to a process for lithium exchange reactions comprising mixing at least two fluids in a microreactor having at least two injection points.

14 Claims, 1 Drawing Sheet

METHOD FOR LITHIUM EXCHANGE REACTIONS

This application is the U.S. National Phase of, and Applicants claim priority from, International Application Number PCT/EP2008/000808 filed 1 Feb. 2008 and European Patent Application bearing Serial No. EP07002522 filed 6 Feb. 2007 each of which are incorporated herein by reference.

BACKGROUND OF THE INVENTION

The present invention relates to a process for lithium exchange reactions in a microreactor.

Lithium exchange reactions are very important reactions in preparative chemistry.

EP-A-1500649 discloses in-situ-quench reactions wherein in a microreactor a lithiumorganic compound ("RG") is mixed with a starting compound ("VP") and a reaction partner ("RP"), the starting material is converted into a reactive intermediate ("ZP"), which reacts in-situ within the microreactor with already present reaction partner ("RP") to the final product.

A persistent aim of the chemical industry is to constantly improve and control chemical reactions. Greater control over reactions may lead to, for example, improvements in safety, increase in reaction product yield and/or purity or in other words improvements of selectivity. This applies to final products or valuable highly reactive intermediates. In particular, greater control over reagent mixing, fluid flow, heat sinking/sourcing and catalytic efficiency is desirable.

A general method which provides such improved control over reactions would therefore be advantageous. Particularly, methods for performing exothermic reactions in large scale in an effective manner are sought-for.

SUMMARY OF THE INVENTION

Figure 1:
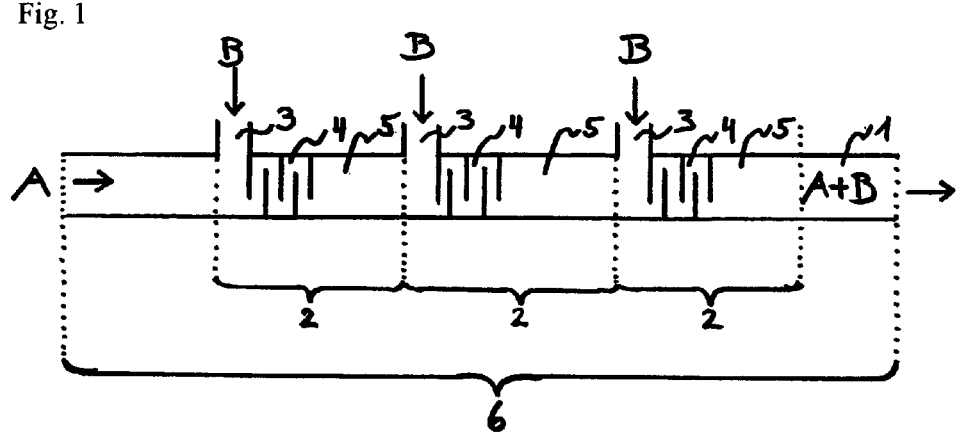
FIG. 1 is a schematic drawing of a microreactor (6) comprising a flow path (1) through the whole microreactor and embedded three reaction regions (2), each reaction region comprising an injection point (3), a mixing zone (4) and a reaction zone (5), wherein a fluid B is fed to a fluid A. According to claim 1 the method for carrying out the reaction any microreactor is suitable having at least two injections points. Preferably the number of injection points (2) is restricted to 10 or less, more preferably to 7 or less.

According to the present invention there is provided a method for carrying out a lithium exchange reaction comprising mixing at least two fluids, one of the at least two fluids comprising a compound able to react with a lithium exchange reagent in a lithium exchange reaction ($1^{st}$ reactant) and another one of the at least two fluids comprising the lithium exchange reagent ($2^{nd}$ reactant). Said mixing is carried out in a microreactor (6) comprising at least one flow path (1) for one of the at least two fluids (A) comprising either the $1^{st}$ or $2^{nd}$ reactant. Said flow path(s) comprise at least two reaction regions (2), wherein each reaction region comprises an injection point (3) for feeding the other one of the at least two fluids (B) comprising either the $2^{nd}$ or the $1^{st}$ reactant, a mixing zone (4) in which the at least two fluids contact each other, and a reaction zone (5). Said microreactor (6) optionally provides one or more additional residence time volumes or has additional residence time volumes attached. In the claimed method one of the at least two fluids comprising either the $1^{st}$ or $2^{nd}$ reactant establishes a first flow and the other one of the at least two fluids comprising either the $2^{nd}$ or $1^{st}$ reactant is injected into said first flow at least at two injection points (3) along said flow path(s) (1) in a way such that at each injection point only a fraction of the amount necessary to reach completion of the lithiation exchange reaction is injected.

Figure 2:
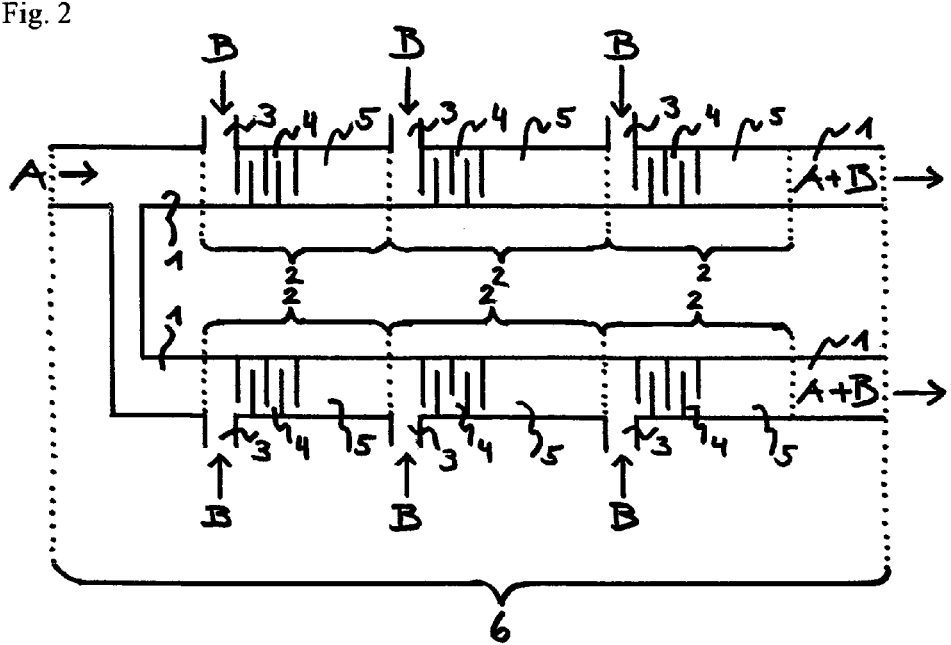
FIG. 2 shows a schematic drawing of a microreactor comprising two such flow paths, wherein the reference signs A, B, and (1) to (5) are as defined in FIG. 1.

FIG. 1 and FIG. 2 show two examples of feeding a flow B at various injection points to a flow A. The microreactor (6) in FIG. 1 comprises one flow path with three injection points, the microreactor (6) in FIG. 2 comprises two flow paths each having three injection points. There maybe more than two flow paths present, as well as more than three injection points in each flow path. Thus, the $2^{nd}$ reactant may be fed at the injections points to a first flow generated by the fluid comprising the $1^{st}$ reactant. From an economical point of view, advantageously the more expensive and/or more reactive reactant is fed as a $2^{nd}$ flow to a $1^{St}$ flow comprising the cheaper and/or less reactive reactant. In most cases the lithium exchange reagent will be at least the more reactive reactant.

Furthermore, there are no structural limits regarding the injection points, the mixing zones and/or the reaction zones. Only for the reason of better understanding of the parts of the microreactor used in the present invention the microreactors in FIG. 1 and FIG. 2 are depicted as a linear strung-out hollow space. Nevertheless, the flow path(s) (1) may be bent tortuously as known in the art. Furthermore, there is no need to maintain the same dimensions in width or length of different mixing zones and/or reaction zones. It is further not necessary to use a microreactor which contains all of the features mentioned above in one physical entity. It is also possible to connect injection points, mixing zones, reaction zones to a flow path externally, optionally cooled or heated.

Feeding only a fraction of the amount necessary to reach completion of the lithium exchange reaction while using more than one injection point leads to an increase of hot spots in the microreactor while in parallel the temperature rise in each hot spot is reduced compared to typical microreactors with only one mixing and reaction zone. In addition, since one of the two compounds is diluted in the first flow comprising the other compound formation of side products is reduced and yields are increased. Thus, the inventive method directly leads to an improved control over reactions.

DETAILED DESCRIPTION OF THE INVENTION

In the present invention independently each of the at least two fluids can be a liquid, a gas or a supercritical fluid. Depending on the mixing properties of the mixing zone it is not necessary that the at least two fluids are miscible. Preferably they are miscible.

Beside the at least one general flow path, at least one injection point, at least one mixing zone and at least one reaction zone a suitable microreactor for the inventive method may comprise additional structural elements such as temperature adjustable retention volumes, temperature adjustable premixing volumes and others known in the state of the art.

It has been found that using a so-called "microreactor" that is a reactor which reaction volumes have dimensions perpendicular to the flow direction of about 10000 μm and less is particularly advantageous for lithium exchange reactions if used with multiple-injection points. According to the present method, improved control over a fluid lithium exchange reaction can be achieved, which can result in significant improvements in reaction product yield and/or purity, as well as other benefits. The reaction starts after contacting the reactive fluids A and B in the mixing zone (3) and continues reacting in a reaction zone (3). In a preferred embodiment the flow path(s) (1) has/have a width in the range of 10-10000 μm and a cross section of 0.1 cm² or less. More preferably the flow path width is in a range of 10-500 μm, or even more preferably in a range of 10-200 μm.

In a further preferred embodiment heat or cooling independently is supplied to the reservoir of agents, injection point(s) (3), the mixing zone(s) (4) and/or the reaction zone(s) (5) or any other structural entity of the microreactor used. Preferably the heat or cooling is supplied by an external source. Said heat or cooling can be supplied to initiate, maintain and/or slow down the reaction. Preferably heat is supplied to initiate and/or maintain the reaction, whereas cooling is supplied to slow down the reaction. In rare cases heat may be supplied to slow down the reaction, whereas cooling may be supplied to initiate and/or maintain the reaction.

In case of fast reactions which react more or less in the mixing zone the reaction zone can be used to adjust the temperature of the reaction mixture before injecting the next fraction of the compound to react in a lithium exchange reaction with the compound already present in the first flow.

Generally, the first flow (1) of fluids containing the reaction product is quenched after being discharged of the microreactor. Fast exothermic reactions which are almost completed when the reaction mixture passed the mixing zone may require additional cooling while passing the reaction zone to suppress side product formation. Performing slow reactions to complete conversion often lead to side products. In a preferred embodiment the product is isolated after quenching of the reaction. In case where the reaction does not reach completion in the mixing zone for several lithium exchange reactions it may be suitable to accommodate the discharged first flow from the reaction zone or the microreactor into a retention volume for further reaction, for other lithium exchange reactions it may be suitable after the last injection point to quench the first flow directly after being discharged of the reaction zone or the microreactor before it reaches completion to avoid over reaction.

We have shown in the examples below that in lithium exchange reactions the yield increases with the number of injection points. Comparing the benefit from each injection zone with the effort to connect or to built-in a further injection zone (new microreactor design, in general increase of required hardware, additional programming work, increased fluid pressure, increased danger of leakage) it has been found, that the inventive method advantageously is carried out with a microprocessor comprising not more than 7 reaction regions (injection points, mixing zones, reaction zones), preferably comprises 3-6 reaction regions.

Further objects, advantages and features may be derived from the depending claims and the described embodiments of the present invention.

In general, a lithium exchange reaction is to be defined as a reaction of a lithium exchange reagent with a compound able to react with said lithium exchange reagent, forming a lithiated product or an intermediate lithium complex which can be used as such for carbon-carbon-coupling reactions or hydrolyzed in water to be transformed into an alcohol. Depending on the electron shifting properties of the organic substituent the lithium exchange reagent is of salt type comprising positive and negative ions or an organolithium compound with a strongly polarized carbon-lithium bond. Thus, a suitable lithium salt is for example lithium di-$C_{1-6}$-alkylamide, lithium tetra- or penta-$C_{1-6}$-alkylpiperidide or lithium hexamethyl-disilazide.

On the other hand a suitable organometallic compound is a compound of formula $$R^1\text{—Li} \qquad\qquad\qquad\qquad\qquad\qquad I,$$

wherein $R^1$ is $C_{1-6}$-alkyl or phenyl.

Preferably the lithium exchange reagent is selected from the group consisting of lithium diisopropylamide, lithium 2,2,6,6-tetramethylpiperidide, lithium 2,2,4,6,6-pentamethyl-piperidide, lithium 1,1,1,3,3,3-hexamethyldisilazide, and a compound of formula I, wherein $R^1$ is as defined above. Even more preferably the lithium exchange reagent is phenyllithium, methyllithium, n-butyllithium, sec-butyllithium, tert-butyllithium or n-hexyllithium.

Reactions i) to iii) depict preferred embodiments of lithium exchange reactions to be performed in a multi-injection microreactor according to the present process.

i) Reacting a lithium exchange reagent as defined above with an acetylene derivative comprising an acidic hydrogen atom of the formula $$R^2\text{—C}\equiv\text{C—H} \qquad\qquad\qquad\qquad II,$$

wherein $R^2$ is a substituent selected from the group consisting of $C_{1-6}$-alkyl, $C_{3-10}$-cycloalkyl, aryl, heteroaryl and aralkyl, and wherein each cycloalkyl, aryl, heteroaryl or aralkyl can carry one or more further substituents selected from the group consisting of $C_{1-6}$-alkyl, $C_{1-6}$-alkoxy, tri-$C_{1-6}$-alkyl silyloxy, to obtain a compound of formula $$R^2\text{—C}\equiv\text{C—Li} \qquad\qquad\qquad\qquad III$$

wherein $R^2$ is as defined above.

Compounds of formula III are important reactive starting materials for further C—C-coupling reactions in the preparative chemistry. It may be directly reacted with another compound. Preferably such reaction is carried out in a further single or multi injection microreactor.

ii) Reacting a lithium exchange reagent as defined above with an aryl halide or heteroaryl halide of formula IV $$R^3\text{—Y} \qquad\qquad\qquad\qquad\qquad\qquad IV,$$

wherein $R^3$ is selected from the group consisting of aryl and heteroaryl, and wherein Y is a halogen atom selected from the group consisting of chlorine, bromine and iodine, to obtain a compound of formula $$R^3\text{—Li} \qquad\qquad\qquad\qquad\qquad\qquad V,$$

wherein $R^3$ is as defined above.

Compounds of formula V are important reactive starting material for further C—C-coupling reactions in the preparative chemistry. They may be directly reacted with another compound. Preferably such reaction is carried out in a further single or multi injection microreactor.

iii) Furthermore, a lithium exchange reagent as defined above can be reacted with an aldehyde, a ketone or an activated carboxylic acid derivative. From the intermediately obtained lithium complex after hydrolization a secondary (from an aldehyde) or tertiary alcohol (from a ketone or an activated carboxylic acid derivative) is obtained, respectively. Optionally, such alcohol may be subject to elimination of the hydroxy group.

Thus, a preferred embodiment comprises reacting a lithium exchange reagent as defined above with an aldehyde, a ketone or an activated carboxylic acid derivative such as an ester, lactone, amide, lactam or an urea derivative of formula $$R^4(CO)R^5 \qquad\qquad\qquad\qquad\qquad\qquad VI,$$

wherein $R^4$ is selected from the group consisting of hydrogen, $C_{1-6}$-alkyl, $C_{1-6}$-alkenyl, $C_{1-6}$-alkynyl, $C_{3-10}$-cycloalkyl, aryl, heteroaryl, aralkyl and dialkylamino, and wherein $R^5$ is $C_{1-6}$-alkyl, alkenyl, alkynyl, $C_{3-10}$-cycloalkyl, aryl, heteroaryl, aralkyl, dialkylamino, di-$C_{3-10}$-cycloalkylamino, diarylamino and diheteroarylamino to obtain an intermediately lithiated compound of formula

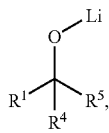

VII wherein $R^1$, $R^4$ and $R^5$ are as defined above, which can be hydrolyzed to the corresponding secondary alcohols of formula

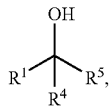

VIII wherein $R^1$, $R^4$ and $R^5$ are as defined above.

The hydroxy group of the compound of formula VIII, wherein $R^1$ is $C_{1-6}$-alkyl, and $R^4$ and $R^5$ are independently selected from the group consisting of $C_{1-6}$-alkyl, alkenyl, alkynyl, $C_{3-10}$-cycloalkyl, can be eliminated to obtain compounds of formulae

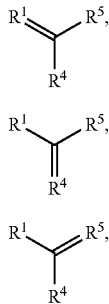

IX

X

XI wherein one proton of the respective residue $R^1$, $R^4$ or $R^5$ is removed and a carbon-carbon double bond is established as depicted in formulae IX to XI.

A preferred example for a suitable compound of formula VI is the urea derivative of formula

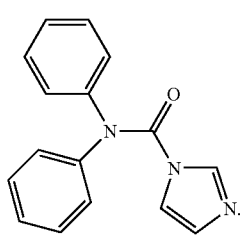

VIa

Here and hereinbelow the term "alkyl" represents a linear or branched alkyl group. By using the form "$C_{1-n}$-alkyl" the alkyl group is meant having 1 to n carbon atoms. $C_{1-6}$-alkyl represents for example methyl, ethyl, propyl, isopropyl, butyl, isobutyl, sec-butyl, tert-butyl, pentyl and hexyl.

Here and hereinbelow the term "cycloalkyl" represents a cycloaliphatic group having 3 carbon atoms or more. $C_{3-10}$-Cycloalkyl represents mono- and polycyclic ring systems such as cyclopentyl, cyclohexyl, cycloheptyl, cyclooctyl, adamantyl or norbornyl.

Here and hereinbelow the term "alkenyl" represents a linear or branched radical comprising a C=C double bond, optionally substituted with one or more halogen atoms and/or optionally substituted $C_{1-6}$-alkyl, $C_{1-6}$-alkoxy or di-$C_{1-6}$-alkylamino groups. Examples are ethenyl, 1-propenyl, 1-butenyl, or isopropenyl.

Here and hereinbelow the term "alkynyl" represents a linear or branched radical comprising a C≡C triple bond, optionally substituted with one or more halogen atoms and/or optionally substituted $C_{1-6}$-alkyl, $C_{1-6}$-alkoxy or di-$C_{1-6}$-alkylamino groups. Examples are ethenyl, 1-propynyl, 1-butynyl, 1-pentynyl.

Here and hereinbelow the term "aryl" represents an aromatic group, preferably phenyl or naphthyl optionally being further substituted with one or more fluorine atoms, $C_{1-6}$-alkyl, $C_{1-6}$-alkoxy, di-$C_{1-6}$-alkylamino and nitro groups.

Here and hereinbelow the term "aralkyl", represents an aromatic group having 7 or more carbon atoms, consisting of an alkyl and an aryl moiety, wherein the alkyl moiety of the aralkyl residue is a $C_{1-8}$ alkyl group and the aryl moiety is selected from the group consisting of phenyl, naphthyl, furanyl, thienyl, benzo[b]furanyl, benzo[b]thienyl, optionally being substituted with one or more halogen atoms, amino groups, and/or optionally substituted $C_{1-6}$ alkyl, $C_{1-6}$ alkoxy or di-$C_{1-6}$-alkylamino groups.

Here and hereinbelow the term "alkoxy" represents a linear or branched alkoxy group. By using the form "$C_{1-n}$-alkoxy" the alkyl group is meant having 1 to n carbon atoms. $C_{1-6}$-alkoxy represents for example methoxy, ethoxy, propoxy, isopropoxy, butoxy, isobutoxy, sec-butoxy, tert-butoxy, pentyloxy and hexyloxy.

Here and hereinbelow the term "di-$C_{1-6}$-alkylamino" represents a dialkylamino group comprising two alkyl moieties independently having 1 to 6 carbon atoms. Di-$C_{1-6}$-alkylamino represents for example N,N-dimethylamino, N,N-diethylamino, N-ethyl-N-methylamino, N-methyl-N-propylamino, N-ethyl-N-hexylamino or N,N-dihexylamino.

Here and hereinbelow the term "dicycloalkylamino" represents a dicycloalkylamino group comprising two cycloalkyl mono- and polycyclic ring moieties independently having 3 carbon atoms or more. Di-$C_{3-10}$-cycloalkylamino represents for example N,N-dicyclopropylamino, N,N-dicyclopentylamino, N,N-dicyclohexylamino, N,N-dicycloheptylamino, N,N-dicyclo-octylamino, N,N-diadamantylamino or N,N-dinorbornylamino, N-cyclopentyl-N-cyclopropylamino and N-cyclohexyl-N-cyclopentylamino.

Here and hereinbelow the term "diarylamino" represents an amino group comprising two aryl moieties. Thus, diarylamino represents for example N,N-diphenylamino or N,N-bis-(4-methyl-phenyl)amino.

Here and hereinbelow the term "diheteroarylamino" represents an amino group comprising two heteroaryl moieties. Thus, diarylamino represents for example N,N-di(pyridin-2-yl)-amino or N,N-bis(4-methyl-2-pyridinyl)amino.

EXAMPLES

The reaction performed in Examples 1.1 to 1.3 and Comparison Examples 1.1 to 1.3 according to preferred reaction embodiment iii) above is:

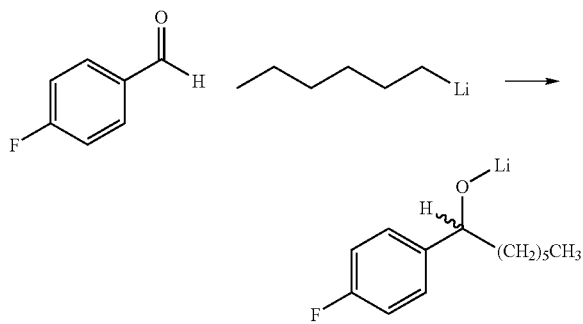

After having passed the microreactor, the effluence of the microreactor is collected in a water reservoir for hydrolysis of the intermediate to the product according to:

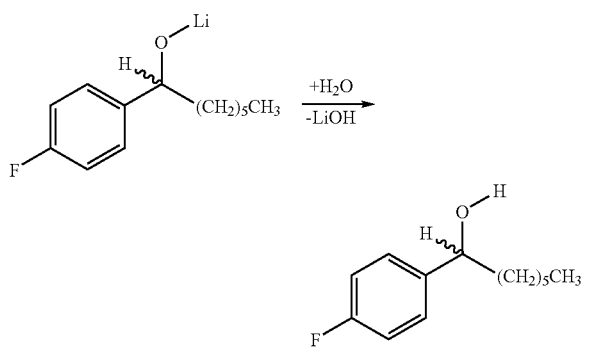

The microreactor (MJ06) used in the example and comparison example was purchased from Corning S.A., Avon, France with integrated cooling of thermal fluid. During the reaction the microreactor is temperature adjusted by immersing in a temperature controlled bath without any additional temperature adjustment system. To facilitate the evaluation of the influence of the number of injection points in all examples the lithium exchange reagent ($2^{nd}$ reactant) is fed to a $1^{st}$ reactant in proportions corresponding to the number of inlet points. With two, three, four, five or six inlet points about 50, 33.3, 25, 20 or 16.6 mol-% of the $2^{nd}$ reactant necessary to reach completion of the reaction respectively are fed at each inlet point. Nevertheless, there is no principal need to fed equal amount at each injection point. Using independently controlled injection systems, for example syringe pumps, or different dimensions of the feed lines is also possible.

By detecting the heat distribution in the micro reactor (comparison example 1), in single-injection ports the occurrence a hot spot with a temperature of about 60 to 70° C. has been be observed. Within the hot spot the solvent is boiling for a short time. Using the multi-injection micro reactor (example 1) prevents boiling of the solvent by avoiding the occurrence of hot spots. In the comparison example 1 six side products could be detected in the reaction mixture, while in example 1 only four side products at lower level could be detected. Although the conversion slightly decreases while using multi-injection ports the selectivity of the reaction and purity of the product increases. Furthermore the occurrence of a hot spot with boiling solvent is accompanied by intense pressure pulsations which could be detected in the coriolis mass flow detector. Such pressure pulsations are detrimental to the fittings and the micro reactor itself. Thus, boiling solvent in the micro reactor does not only lead to more side products but also increases the risk of damaging the micro reactor even up to explosions.

General Conditions:

In all Examples an Comparison examples Feed-1 was 4-fluorobenzaldehyde (4F-BZA) (20 wt %) in THF (80 wt %) with about 29 g/min, fed by a gear pump (Ismatec, Wertheim-Mondfeld, Germany) with coriolis flow controller. Correspondingly in all cases Feed-2 was n-hexyllithium (HexLi) (33 wt %) in Hexane (67 wt %) controlled by a SiProcess syringe pump (Siemens, Germany). The stoichiometry of HexLi to 4-F-BZA was set to 1.00. The flow rate Feed-1 was 29.0 g/min, the flow rate of Feed-2 was about 9.0 g/min with one injection point and about 3.0 g/min when split into 3 flows. The temperature was set to: −30, −20 or −10° C.

The multi-injection microreactors used comprises a main injection port, 4 reaction regions (each comprising one injection point, one mixing zone and one reaction zone of 1.08 mL internal reaction volume). Typically the $1^{st}$ reactant is fed through the main port and the $2^{nd}$ reactant through one or more of the additional injections points (Port-1, Port-2, Port-3 and Port-4). Each port can be opened or closed individually from the other ports. To operate the microreactor as a single-injection micro reactor, only port-1 is used.

Example 2 was carried out in essentially the same way than Example 1 with the difference that an additional residence module (RT) (Coil-H1) was added that was operated at −30 to +10° C. to complete the reaction. The obtained yields are higher than in example 1, without loss of selectivity.

Example 1

Feed-1 was fed through the main port. Feed-2 was fed in equivalent proportions through Port-1, Port-2 and Port-3, while Port-4 was closed, thus the microreactor actually had 3 working mixing zones. Three runs were performed. The average results are shown in Table 1.

Comparison Example 1

Feed-1 was fed through the main port. Feed-2 was fed in equivalent proportions through Port-1. Port-2, Port-3 and Port-4 were closed, thus the microreactor actually had only 1 working mixing zone. Three runs were performed. The average results are shown in Table 1.

TABLE 1

| | T-MR [° C.] | Product [area %] | Byproducts [area %] | Conversion [area %] | Selectivity [area %] |
|---|---|---|---|---|---|
| Example 1.1 | −30 | 89.5 | 3.5 | 93.0 | 96.2 |
| Example 1.2 | −20 | 90.2 | 5.5 | 95.7 | 94.3 |
| Example 1.3 | −10 | 91.7 | 6.1 | 93.0 | 96.2 |
| Comp. Ex. 1.1 | −30 | 91.9 | 7.3 | 99.2 | 92.6 |
| Comp. Ex. 1.2 | −20 | 92.5 | 7.0 | 99.5 | 92.9 |
| Comp. Ex. 1.3 | −10 | 91.7 | 7.8 | 99.5 | 92.2 |

Not shown are residues of the starting material. The results show that although the conversion rate under the multi injection conditions of example 1 is somewhat lower than under the single-injection conditions of comparison Example 1, the byproduct/product rate of 7.6% in Comparison Example 1 could be lowered to 4.4% to 6.6% in Example 1. T-MR is the temperature of the fluid for thermal adjustment of the microreactor.

Example 2

Feed-1 was fed through the main port. Feed-2 was fed in equivalent proportions through Port-1, Port-2 and Port-3, while Port-4 was closed, thus the microreactor actually had 3 working mixing zones. The results are shown in Table 2.

Only 4 byproducts could be detected compared to 6 in the comparison examples.

TABLE 2

|  | T-MR [° C.] | T-RT [° C.] | Product [area %] | Byproducts [area %] | Conversion [area %] | Selectivity [area %] |
|---|---|---|---|---|---|---|
| Example 2.1 | −30 | −30 | 90.6 | 4.3 | 94.9 | 96.0 |
| Example 2.2 | −20 | −20 | 91.5 | 5.1 | 96.5 | 95.3 |
| Example 2.3 | −30 | −10 | 92.4 | 3.6 | 96.4 | 96.3 |
| Example 2.4 | −30 | ±0 | 93.1 | 4.3 | 97.7 | 95.8 |
| Example 2.5 | −30 | +10 | 94.4 | 4.3 | 99.1 | 95.7 |

T-MR is the temperature of the fluid for thermal adjustment of the microreactor.
T-RT is the temperature of the fluid for thermal adjustment of the retention module.

The invention claimed is:

1. A method for carrying out a lithium exchange reaction comprising mixing at least two fluids, one of the at least two fluids comprising, a compound able to react with a lithium exchange reagent in a lithium exchange reaction ($1^{st}$ reactant), and another fluid comprising a lithium exchange reagent ($2^{nd}$ reactant), said mixing taking place in a microreactor comprising at least one flow path for one of the at least two fluids comprising either the $1^{st}$ or $2^{nd}$ reactant, said flow path(s) comprising at least two reaction regions, each reaction region comprising an injection point for feeding the other one of the two fluids comprising either the $2^{nd}$ or $1^{st}$ reactant, a mixing zone in which the at least two fluids contact each other and a reaction zone, and wherein the microreactor optionally provides one or more additional residence time volumes or has additional residence time volumes attached, and wherein in said method one of the at least two fluids comprising either the $1^{st}$ or $2^{nd}$ reactant establishes a first flow and wherein the other one of the at least two fluids comprising either the $2^{nd}$ or $1^{st}$ reactant is injected into said first flow at least at two injection points along said flow path(s) in a way such that at each injection point less than the total amount necessary to reach completion of the lithium exchange reaction is injected.

2. The method of claim 1, wherein the flow path(s) has/have a width in the range of 10 to 10000 μm and a cross section of 0.1 cm² or less.

3. The method of claim 2, wherein the flow path width is in a range of 10 to 500 μm.

4. The method of claim 3, wherein the flow path width is in a range of 10 to 200 μm.

5. The method of claim 1, wherein heat or cooling independently is supplied to the injection point(s), the mixing zone(s) and/or the reaction zone(s).

6. The method of claim 5, wherein heat or cooling is supplied to initiate, maintain and/or slow down the reaction.

7. The method of claim 6, wherein heat is supplied to initiate and/or maintain the reaction.

8. The method of claim 6, wherein cooling is supplied to slow down the reaction.

9. The method of claim 1, wherein the microreactor comprises 3-6 reaction regions.

10. The method of claim 1, wherein in slow reactions the reaction is quenched after the last reaction zone before it reaches completion.

11. The method of claim 1, wherein the lithium exchange reagent ($2^{nd}$ reactant) is selected from the group consisting of lithium di-$C_{1-6}$-alkylamide, lithium tetra- or penta-$C_{1-6}$-alkylpiperidide, lithium hexamethyldisilazide and a compound of formula $$R^1\text{—Li} \qquad \text{I,}$$

wherein $R^1$ is $C_{1-6}$-alkyl or phenyl.

12. The method of claim 1, wherein the $1^{st}$ reactant is a compound of formula $$R^2\text{—C≡C—H} \qquad \text{II,}$$

wherein $R^2$ is a substituent selected from the group consisting of $C_{1-6}$-alkyl, $C_{3-10}$-cyclo-alkyl, aryl, heteroaryl and aralkyl, and wherein each cycloalkyl, aryl, heteroaryl or aralkyl can carry one or more further substituents selected from the group consisting of $C_{1-6}$-alkyl, $C_{1-6}$-alkoxy and tri-$C_{1-6}$-alkylsilyloxy.

13. The method of claim 1, wherein the $1^{st}$ reactant is a compound of formula $$R^3\text{—Y} \qquad \text{IV,}$$

wherein $R^3$ is aryl or heteroaryl, and wherein Y is a halogen atom selected from the group consisting of chlorine, bromine and iodine.

14. The method of claim 1, wherein the $1^{st}$ reactant is a compound of formula $$R^4(CO)R^5 \qquad \text{VI,}$$

wherein $R^4$ is selected from the group consisting of hydrogen, $C_{1-6}$-alkyl, alkenyl, alkynyl, $C_{3-10}$-cycloalkyl, aryl, heteroaryl, aralkyl and dialkylamino, and wherein $R^5$ is $C_{1-6}$-alkyl, alkenyl, alkynyl, $C_{3-10}$-cycloalkyl, aryl, heteroaryl, aralkyl, dialkylamino, di-$C_{3-10}$cycloalkylainino, diarylamino and diheteroarylamino.

* * * * *

UNITED STATES PATENT AND TRADEMARK OFFICE
CERTIFICATE OF CORRECTION

PATENT NO. : 8,198,487 B2
APPLICATION NO. : 12/524910
DATED : June 12, 2012
INVENTOR(S) : Roberge et al.

It is certified that error appears in the above-identified patent and that said Letters Patent is hereby corrected as shown below:

IN THE SPECIFICATION:

Column 2, line 14:

Now reads: "There maybe more"

Should read: -- There may be more --

Column 3, line 35:

Now reads: "In case where"

Should read: -- In cases where --

Column 3, line 47:

Now reads: "or to built-in a further"

Should read: -- or to build-in a further --

Column 7, line 47:

Now reads: "need to fed"

Should read: -- need to feed --

Signed and Sealed this
Ninth Day of July, 2013

Teresa Stanek Rea
*Acting Director of the United States Patent and Trademark Office*